(12) United States Patent
Andreasson et al.

(10) Patent No.: US 6,816,569 B2
(45) Date of Patent: Nov. 9, 2004

(54) X-RAY DIAGNOSTICS INSTALLATION FOR MAMMOGRAPHY EXAMINATIONS

(75) Inventors: Jesper Andreasson, Järfälla (SE); Ann-Sofi Hoff, Stockholm (SE); Stefan Karlsson, Sollentuna (SE)

(73) Assignee: Siemens Aktiengesellschaft, Münich (DE)

( * ) Notice: Subject to any disclaimer, the term of this patent is extended or adjusted under 35 U.S.C. 154(b) by 117 days.

(21) Appl. No.: 10/268,152

(22) Filed: Oct. 10, 2002

(65) Prior Publication Data

US 2003/0076923 A1 Apr. 24, 2003

(30) Foreign Application Priority Data

Oct. 18, 2001 (SE) .............................................. 0103474

(51) Int. Cl.⁷ ................................................. A61B 6/04
(52) U.S. Cl. ........................................ 378/37; 378/177
(58) Field of Search .................... 378/37, 181, 177, 378/208

(56) References Cited

U.S. PATENT DOCUMENTS 3,743,843 A * 7/1973 Reser et al. ................... 378/27
4,613,982 A    9/1986 Dornheim et al.
4,930,143 A    5/1990 Lundgren et al.
4,989,227 A    1/1991 Tirelli et al.
5,050,197 A *  9/1991 Virta et al. .................... 378/37
5,148,466 A    9/1992 Fajac

FOREIGN PATENT DOCUMENTS

WO    WO 88/01847    3/1988

* cited by examiner

Primary Examiner—Edward J. Glick
Assistant Examiner—Elizabeth Keaney
(74) Attorney, Agent, or Firm—Schiff Hardin LLP

(57) ABSTRACT

An X-ray diagnostics installation for mammography examinations has an arm for an X-ray tube, a holder for an image receiver and a subject table. The holder and the subject table are laterally adjustable relative to one another. A compression plate arranged between the X-ray tube and the subject table is connected to and displaceable along the arm. The arm is rotatable around a horizontal shaft attached to a stand. In order to maintain the image receiver located in the X-ray field simply and inexpensively given rotation of the subject table or of the image receiver from a vertical attitude into a lateral attitude, the holder for the image receiver is connected to the arm, and the subject table is laterally displaceable relative to the holder.

1 Claim, 3 Drawing Sheets

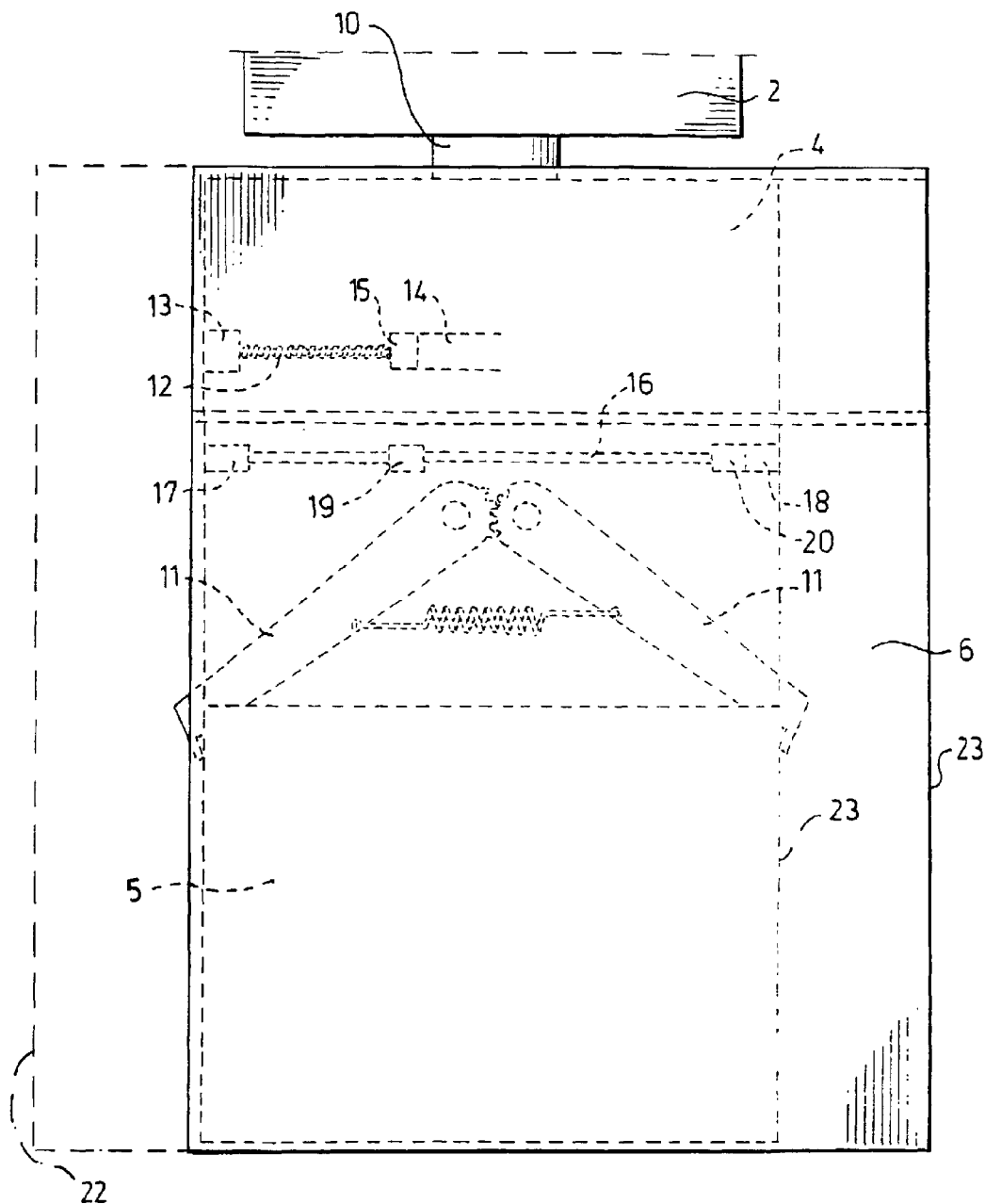

X-RAY DIAGNOSTICS INSTALLATION FOR MAMMOGRAPHY EXAMINATIONS

BACKGROUND OF THE INVENTION

1. Field of the Invention

The present invention is directed to an X-ray diagnostic installation for mammography examination of the type having an arm for an X-ray tube, a holder for an image receiver and a subject table, the holder and the subject table being laterally adjustable relative to one another, as well as having a compression plate arranged between the X-ray tube and the subject table, the compression plate being connected to and displaceable along the arm, and wherein the arm is rotatable around a horizontal shaft attached in a stand.

2. Description of the Prior Art

It is advantageous in a mammography examination when the size of the image receiver is adapted to the size of the subject table. In those instances wherein the image receiver is an X-ray film applied in a cassette, there are two standard cassette sizes in the marketplace, namely a larger X-ray film cassette having the dimensions 24×30 cm and a smaller X-ray film cassette having the dimensions 18×24 cm.

One possibility that is practiced is disclosed in U.S. Pat. No. 4,613,982, is to have a subject table for each cassette size, the width of the subject table corresponding to the width of the cassette. In this way, the user can change between the cassette sizes dependent on the size of the subject. Having multiple of subject tables, however, is comparatively expensive and changing the subject table can be time-consuming.

The reason why the width of the cassette or of the X-ray film should be the same as the width of the subject table is so that, in a lateral exposure, the subject table and thus the X-ray film as well can be displaced into the armpit of the patient so that as much breast tissue as possible is imaged.

In conjunction with an X-ray diagnostic installation of the type initially described, that is disclosed in U.S. Pat. No. 4,989,227, a proposal is made to simplify the mammography examination and to reduce the costs by only one subject table being employed for the X-ray film cassettes that differ in size. The subject table, which is secured to the arm for the X-ray tube, has a width that corresponds to the width of the larger of the two standard cassettes. In a lateral exposure, the desired imaging of the breast tissue is therefore established with a larger X-ray film cassette present in the subject table.

Given employment of the smaller cassette, the arrangement in the subject table disclosed in said U.S. Pat. No. 4,989,227 can be used to shift it into three fixed positions, namely a centered position wherein the cassette is attached so as to be spaced from the end sides of the table, a position wherein the one end side of the cassette lies along one side of the subject table, and a position wherein the other end side of the cassette lies along the other side of the subject table.

For a vertical exposure of the breast, the cassette is attached in the centered position. For a lateral exposure, the subject table is rotated around the horizontal shaft with the above-described arm so that the subject table is pushed into the armpit of the patient. In this position, the cassette in the subject table is shifted into a position wherein the upper end side of the cassette lies along the upper side of the subject table. In combination with a displacement of the cassette in the subject table, the radiation field of the X-ray tube no longer covers the entire surface of the cassette or the X-ray receiver. For a lateral exposure, a setting of the diaphragms of the X-ray tube must be undertaken anew, which is relatively time-consuming. This can be unpleasant for the patient and somewhat painful since the breast is clamped between the subject table and the compression plate.

SUMMARY OF THE INVENTION

An object of the present invention is to provide an X-ray diagnostic installation of the type initially described wherein the image receiver can remain located in the X-ray field with simple and thus inexpensive means given rotation of the subject table or of the image receiver from a vertical attitude into a lateral attitude.

This object is achieved in an X-ray diagnostics installation of the initially described type wherein the holder for the image receiver is connected to the arm, and the subject table is fashioned to be laterally displaceable relative to the holder. Because the holder for the image receiver is connected to the arm, the image receiver remains in the X-ray field in all positions of the arm. In conjunction with a lateral exposure, i.e. when the image receiver is pushed into the patient's armpit, the subject table is shifted into a position wherein the upper side thereof lies along the short side of the image receiver. An exposure can now be made relatively quickly.

DESCRIPTION OF THE DRAWINGS

FIG. 3 is a further plan view of a subject table according to FIG. 2.

DESCRIPTION OF THE PREFERRED EMBODIMENTS

Figure 1:
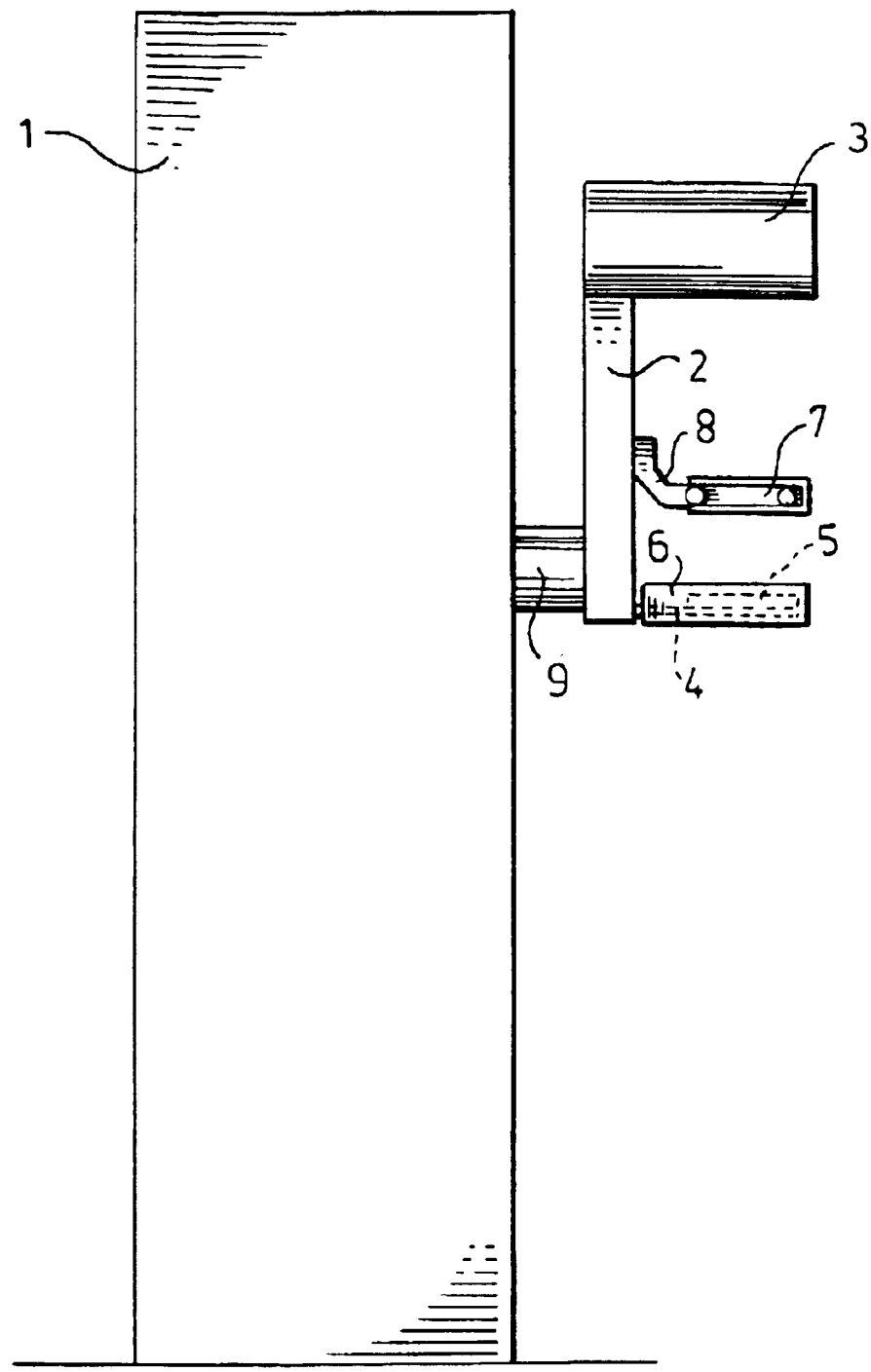
FIG. 1 is a side view of an X-ray diagnostic installation of the invention for mammography examinations.

FIG. 1 schematically shows an X-ray diagnostic installation for mammography examinations having a stand 1 that carries an arm 2 for an X-ray tube 3. The arm 2 also carries a holder 4 for an image receiver 5 as well as a subject table 6. The holder 4 and the subject table 6 are described in greater detail in conjunction with FIGS. 2 and 3. A compression plate 7 is arranged between the X-ray tube 3 and the subject table 6, the compression plate 7 being connected via a console 8 to the arm 2 so as to be displaceable along the arm 2. The arm 2 is rotatably connected to the stand 1 via a horizontal shaft 9.

Figure 2:
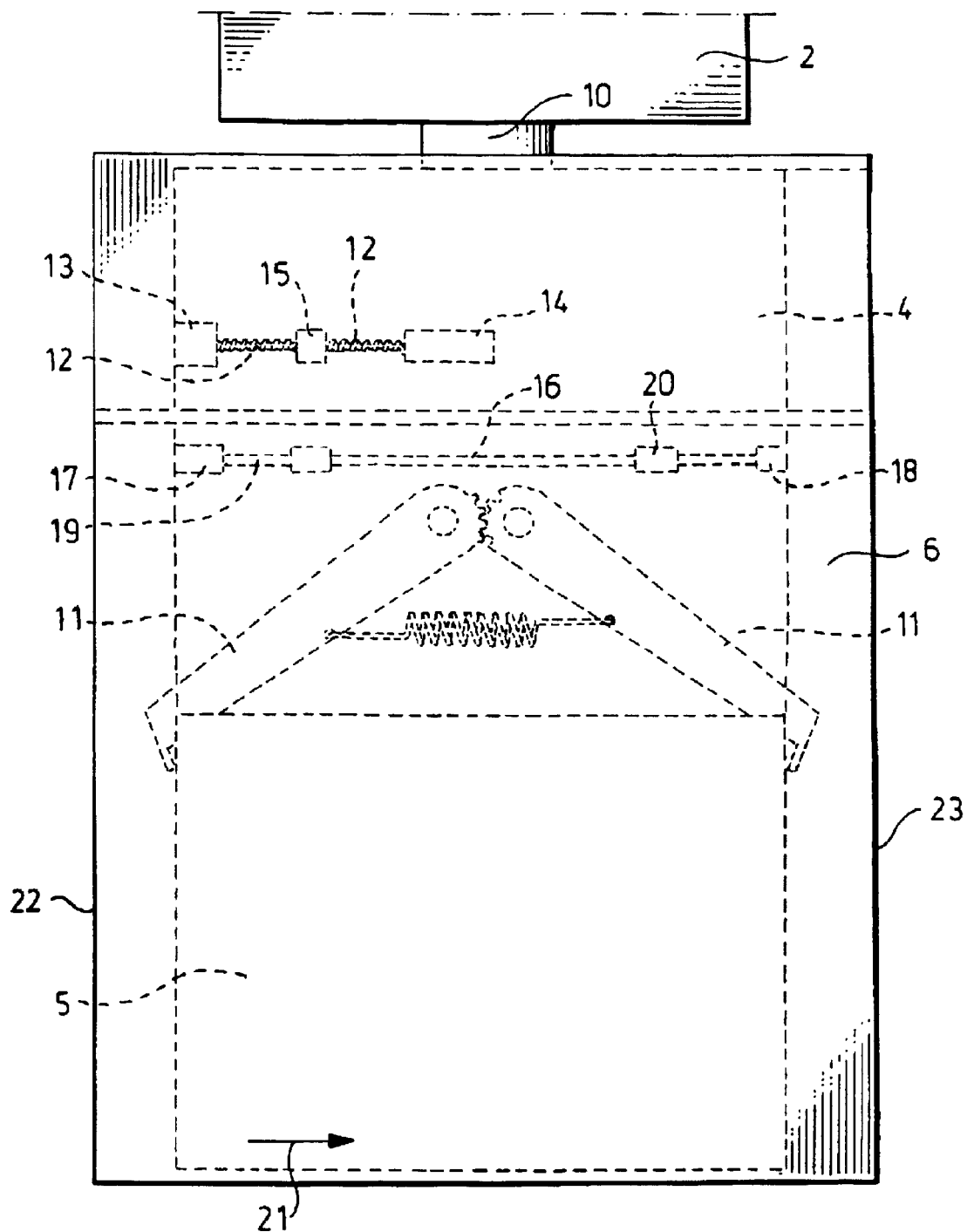
FIG. 2 is a plan view of an subject table of the X-ray diagnostic installation of FIG. 1.

FIG. 2 shows, in a plan view, that the holder 4 of the image receiver 5 is connected to the arm 2 via a shaft 10. The image receiver 5 is a cassette for an X-ray film in this exemplary embodiment. The X-ray film cassette 5 shown in FIG. 2 is the smaller of the cassettes described above.

The holder 4 preferably is a plate with a width that corresponds to the width of the smaller of the two cassettes. The cassette 5 is clamped to the holder 4 with two spring-loaded gripper arms 11 arranged at the holder 4. The holder 4 is provided with a screw 12 that is arranged in the transverse direction of the holder 4. One end 13 of the screw 12 is connected to the holder 4 and the other end thereof is connected to a motor 14. The screw 12 also is connected to a sleeve 15 provided with an internal thread that is in turn secured to the table.

The holder 4 also is provided with a rod 16 that is arranged parallel to the screw 12 and that proceeds along the width of the holder 4. The ends of the rod 16 are firmly connected to the holder 4 via detents 17, 18. Further, sleeves 19, 20 are provided that are displaceable along the rod 16, the sleeves being secured to the subject table 6.

For a vertical exposure of a breast of a patient, the breast is placed onto the subject table 6. Subsequently, the breast is compressed by the compression plate 7, and an exposure is made. In conjunction with a rotation of the holder 4 or of the subject table 6 around the shaft 9 by means of the arm 2 into a lateral position for a lateral exposure, for example of the left armpit of the patient, the subject table 6 is shifted relative to the holder 4 in the direction of the arrow 21 to such an extent until the side 22 of the subject table 6 lies along the side of the holder 4 and the narrow side of the cassette 5. This is shown in FIG. 3. A lateral displacement of the subject table 6 in relationship to the holder 4 and the cassette 5 ensues by the motor 14 rotating the screw 12 such that the sleeve 15 and thus the subject table 6 are displaced in the longitudinal direction of the screw 12. When the sleeve 20, which is simultaneously shifted along the rod 16, has reached the detent 18, then the desired displacement of the subject table 6 has ensued. An exposure can ensue after the compression plate 7 has compressed the beast in this lateral position.

In conjunction with a lateral exposure of the right armpit of the patient, the subject table 6 is shifted in relationship to the holder 4 into a position wherein the other side 23 of the subject table 6 lies along the other side of the holder 4 and the other narrow side of the cassette 5. This is accomplished by the motor 14 rotating the screw 12 in the opposite direction compared to that described above, so that the sleeve 15 and the subject table are displaced until the sleeve 19, which runs along the rod 16, reaches the detent 17.

Such a position of the subject table 6 is shown in FIG. 3 with dot-dash contours thereof.

Because the holder 4 and the cassette 5 have not moved in relationship to the X-ray tube 3 in conjunction with the described motions, it is not necessary to undertake what is usually a time-consuming adjustment of the radiation field, which should cover the cassette 5 and the X-ray film, by means of the existing X-ray diaphragms.

The motor 14 can be a stepping motor that, when switched on, displaces the subject table 6 into a middle position or centered position for a vertical exposure and into an extreme right position or an extreme left position in relationship to the holder 4 for lateral exposures, as desired.

In accordance with the invention, the displacement of the subject table 6 relative to the holder 4 alternatively can ensue manually, with the subject table being arrested in the described positions by locking devices that are known and therefore not described in greater detail.

As an alternative to an X-ray film cassette, the image receiver can be an image disk or CCD disk.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray mammography examination apparatus comprising:

an X-ray tube which emits an X-ray beam;

an image receiver on which said X-ray beam is incident, said image receiver having two opposite lateral receiver sides;

a holder for said image receiver;

a subject table adapted to receive a breast for producing an exposure with said X-ray tube and said image receiver, said subject table having two opposite lateral table sides and being laterally displaceable from one centered position into two lateral positions relative to said holder and said image receiver, said lateral receiver sides in said centered position each being disposed at the same distance from a corresponding one of said lateral table sides, and one of said lateral receiver sides in the respective lateral positions being substantially flush with a corresponding lateral table side;

a compression plate disposed between said X-ray tube and said subject table adapted to compress a breast on said subject table;

an arm to which said X-ray tube, said holder and said compression plate are attached; and a stand having a horizontal shaft to which said arm is mounted so as to be rotatable around said horizontal shaft.

* * * * *